(12) United States Patent
Villette

(10) Patent No.: US 6,245,043 B1
(45) Date of Patent: Jun. 12, 2001

(54) INJECTOR FOR MEDICAL USE

(76) Inventor: Alain Villette, Les Vannes, St. Pierre des Echaubrognes 79700 (FR)

( * ) Notice: Subject to any disclaimer, the term of this patent is extended or adjusted under 35 U.S.C. 154(b) by 0 days.

(21) Appl. No.: 09/355,356

(22) PCT Filed: Nov. 27, 1998

(86) PCT No.: PCT/FR98/02551

§ 371 Date: Jul. 27, 1999

§ 102(e) Date: Jul. 27, 1999

(87) PCT Pub. No.: WO99/27984

PCT Pub. Date: Jun. 10, 1999

(30) Foreign Application Priority Data

Dec. 3, 1997 (CA) ................................................ 2223659

(51) Int. Cl.$^7$ .................................................. A61M 37/00
(52) U.S. Cl. .......................................................... 604/154
(58) Field of Search .................................. 604/154, 187, 604/155, 65–67, 188; 128/DIG. 1, 12, 13; 81/9.22; 30/362, 366; 606/184, 185, 167, 170

(56) References Cited

U.S. PATENT DOCUMENTS

| | | | |
|---|---|---|---|
| 3,656,480 | * | 4/1972 | Rubricius ............................. 128/218 |
| 4,465,474 | * | 8/1984 | Mardorf et al. ..................... 604/154 |
| 4,620,848 | * | 11/1986 | Sutherland et al. ................. 604/154 |
| 4,787,893 | * | 11/1988 | Villette ................................ 604/188 |
| 4,796,624 | * | 1/1989 | Trott et al. .......................... 81/9.22 |
| 4,914,988 | * | 4/1990 | Chang ................................. 81/9.22 |
| 4,952,205 | * | 8/1990 | Mauerer et al. ..................... 604/154 |
| 5,021,046 | * | 6/1991 | Wallace ............................... 604/97 |
| 5,139,484 | * | 8/1992 | Hazon et al. ........................ 604/154 |
| 5,173,050 | | 12/1992 | Dillon ................................. 433/165 |
| 5,236,416 | * | 8/1993 | McDaniel et al. .................. 604/155 |
| 5,244,461 | * | 9/1993 | Derlien .............................. 604/65 |
| 5,290,261 | | 3/1994 | Smith, Jr. et al. ................. 604/234 |
| 5,300,029 | * | 4/1994 | Denance ............................. 604/117 |
| 5,368,572 | * | 11/1994 | Shirota ............................... 604/155 |
| 5,586,473 | * | 12/1996 | Choy .................................. 81/9.22 |
| 5,672,155 | * | 9/1997 | Riley et al. ......................... 604/154 |
| 5,735,868 | * | 4/1998 | Lee ...................................... 606/189 |

FOREIGN PATENT DOCUMENTS

| | | |
|---|---|---|
| 2418652 | 9/1979 | (FR) . |
| 2581548 | 11/1986 | (FR) . |
| 2716375 | 8/1995 | (FR) . |
| 2067076 | 7/1981 | (GB) . |
| WO 9208410 | 5/1992 | (WO) . |

* cited by examiner

*Primary Examiner*—Manuel Mendez
(74) *Attorney, Agent, or Firm*—Duane, Morris & Heckscher LLP

(57) ABSTRACT

An injector for medical use, in particular with semisolid substances, the injector comprising a case and at least one injection electric motor pressing against a piston acting on the moving end of a cartridge, the motor being movable in translation inside the body in order to exert force on the axis.

4 Claims, 3 Drawing Sheets

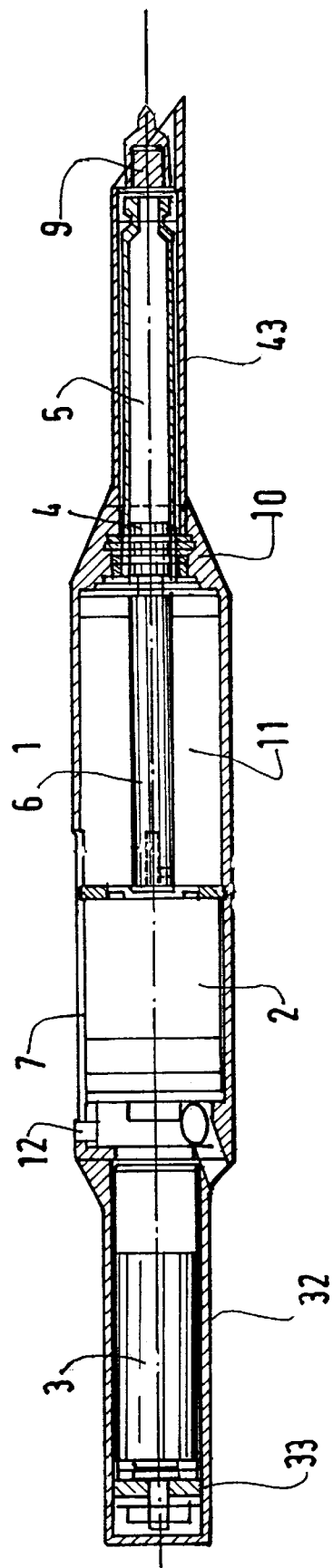
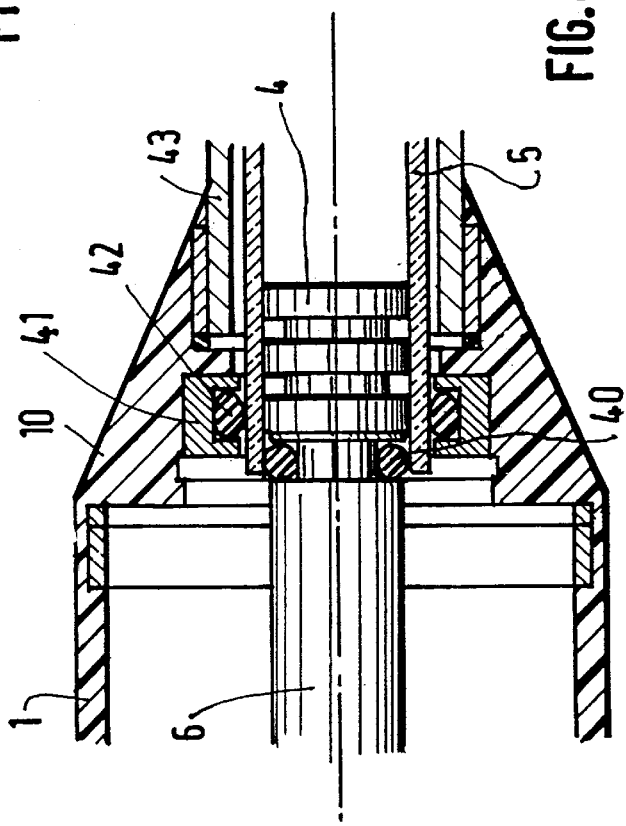

INJECTOR FOR MEDICAL USE

The present invention relates to an injector for use in dentistry, for performing intramedullary or intradiploic injections of anesthetic or for performing injections into soft tissue.

BACKGROUND OF THE INVENTION

In dental surgery, the conventional solution is to use a syringe to inject a determined quantity of liquid anesthetic into the gum of the patient at a certain distance from the tooth that is to be attended to. However, that procedure suffers from drawbacks such as a considerable latency time between injection and anesthetic action, and of a quantity of anesthetic being injected that is larger than necessary. To remedy those drawbacks, proposals have already been made to provide intradiploic anesthesia whereby injection takes place directly into the marrow of the maxillary bone after passing through the cortical substance. The action of the anesthetic is thus more effective. To this effect, it is known to cause the injection needle to rotate so as to facilitate penetration of the needle through the cortical substance which is a hard region. After which a piston is displaced which bears against the moving end of the cartridge containing the anesthetic.

Proposals have already been made, in particular in U.S. Pat. No. 5,173,050 to perform such anesthesia in two stages. Initially the cortical substance is pierced, after which the injector is withdrawn and the perforation needle is replaced by an injection needle. However it is very difficult to find the perforation again so as to proceed with injection.

An injector that enables such anesthesia to be performed without needing to remove the perforation needle is described in FR-A-2 581 548. In that patent, the means for rotating the cartridge and for moving the moving end of the cartridge are constituted by two micro-motors, with the mechanical link between the cartridge and the motor for rotating said cartridge being obtained by means of gears. The same applies to driving the piston which is obtained via stepdown gearing. It is thus possible to obtain injection that is continuous and regular, which was not the case with hand syringes. However, it turns out that those drives give rise to undesirable noise, since the motor is rotating at very high speeds of several tens of thousands of revolutions per minute.

OBJECTS AND SUMMARY OF THE INVENTION

The present invention thus seeks to mitigate those drawbacks. It is based on the idea that all of the forces to be transmitted need to be transmitted on the axis of the injector while avoiding any mechanical transmission which quite often gives rise to eccentricity in the applied forces, giving rise to breakage of the cartridge.

According to the invention, an injector having one motor for rotating a piston and a second motor for driving said piston in translation, the piston being in contact with the moving end of a cartridge which is fixed in removable manner to the body of the injector, is wherein the motor for driving the piston in translation lies on the same axis as the piston and is mounted inside the cylindrical body of the injector, drive in translation being the result of the drive shaft driving a screw which co-operates with an inside thread of the body of the injector, with operation of the motors being under the control of an electronics card.

Preferably, the drive screw of the motor has a hub through which fixing screws pass.

The force applied to the end of the cartridge or container is accurately coaxial therewith and the drive in translation takes place without slip.

According to another characteristic of the invention, the control of the injection motor is programmed so that the volume injected is progressive, thereby very significantly reducing the pain.

BRIEF DESCRIPTION OF THE DRAWINGS

Other characteristics and advantages of the invention appear from the following description of particular embodiments, given purely as non-limiting examples, and with reference to the drawings in which:

FIG. 1 is a cross-section of a dental injector of the invention;

FIG. 4 is a fragmentary section view showing how the cartridge is mounted in the dental anesthetic injector;

MORE DETAILED DESCRIPTION

Figure 2:
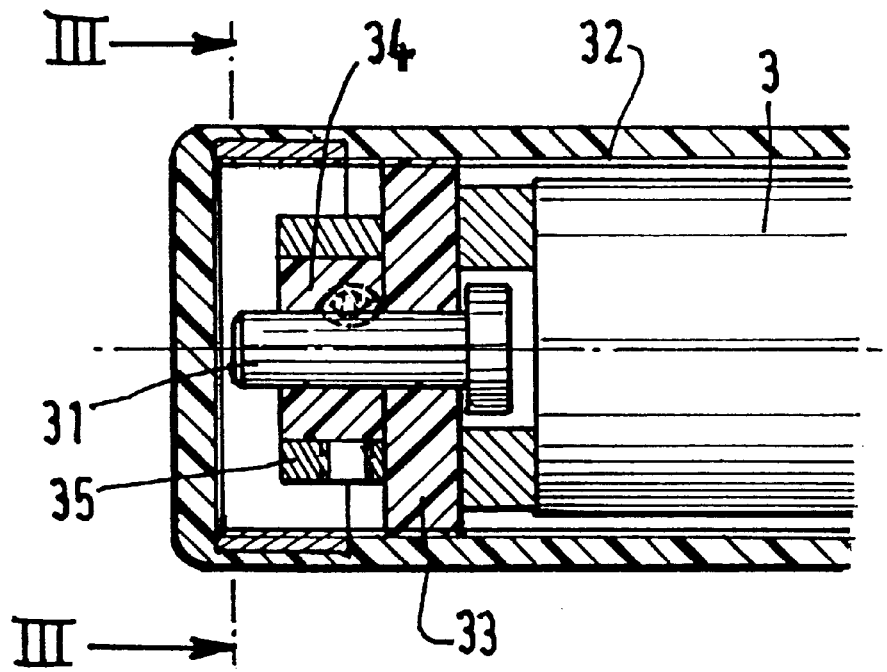
FIG. 2 is a detail view of how the injection motor is mounted.

FIG. 1 shows an injector for dental anesthesia of the intradiploic type, i.e. requiring the needle to penetrate into a bone prior to injection. Under such circumstances, in addition to providing a motor for axial displacement or translation that serves to inject the anesthetic, it is also necessary to provide an additional motor capable of imparting rotary motion to the needle so as to facilitate passing through the bone prior to performing injection proper.

In FIG. 1, there can be seen a hollow cylindrical body 1 containing a motor 2 for rotating the cartridge and the needle 9, and a motor 3 for moving the motor 2 in axial displacement, and also a piston 6 whose front end bears against the sliding end wall 4 of the cartridge 5. A partially frustoconical housing 10 is mounted on the front of the body 1 to hold and guide the cartridge 5.

In accordance with the invention, the rotation motor 2 lies on the same axis as the injection motor 3, as the cartridge 5 (or supply of anesthetic), and as the needle 9. As can be seen in FIG. 1, the motor 2 is placed in front of the injection motor 3 in a cage 11, and its outlet shaft is mechanically connected to the piston 6. A cartridge 5 is secured at the front end of the injector in a housing 10 provided for this purpose, and a needle 9 is fixed at the front of the cartridge 5, with the rear end of the needle passing through the front gasket of the cartridge to establish communication between the cartridge 5 and the channel inside the needle 9. The housing 10 forms a bearing for the cartridge, and consequently for the needle. When the motor 2 is powered it thus normally serves to rotate the needle 9, thereby facilitating perforation of the bone. Initially, it remains stationary, with the pressure required coming from the pressure exerted by the dental surgeon.

Thereafter, setting the shaft 31 of the motor 3 into rotation gives rise to displacement from a rest position, on the left in FIG. 1, towards the right.

Figure 3:
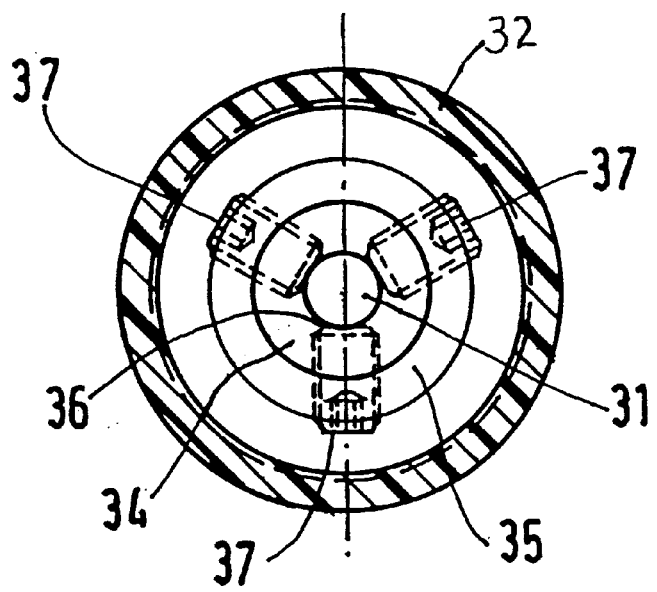
FIG. 3 is a section on line III—III of FIG. 2.

As can be seen more clearly in FIG. 2, which is a detail view on a larger scale of the rear portion of the injector, and also from FIG. 3, inside the body 1 of the injector, and in the rear portion thereof, there is mounted an internally threaded sheath or sleeve 32. A disk-shaped screw 33, advantageously made of DELRIN (registered trademark), has an external thread at the same pitch as the internal thread of the sleeve and is suitable for moving therein when rotated. The screw 33 is extended rearwards by a hub 34. The hub is surrounded by a metal ring 35. The screw 33 is rotated by means of a mechanical link between the drive shaft 31 and the hub 34 of the screw 33. To this end, the smooth shaft 31 has a flap 36. A radial screw 37 bears against the flap, which screw passes through the metal ring 35 and the hub 34 so as to come into contact with the drive shaft 31. Given that the force to be transmitted is large, it is preferable to provide two more radial screws 37, each at an angle of 120° to the adjacent screws. The torque due to rotation of the drive shaft 31 is thus transmitted without running the risk of breakage at the screw 33.

Figure 5:
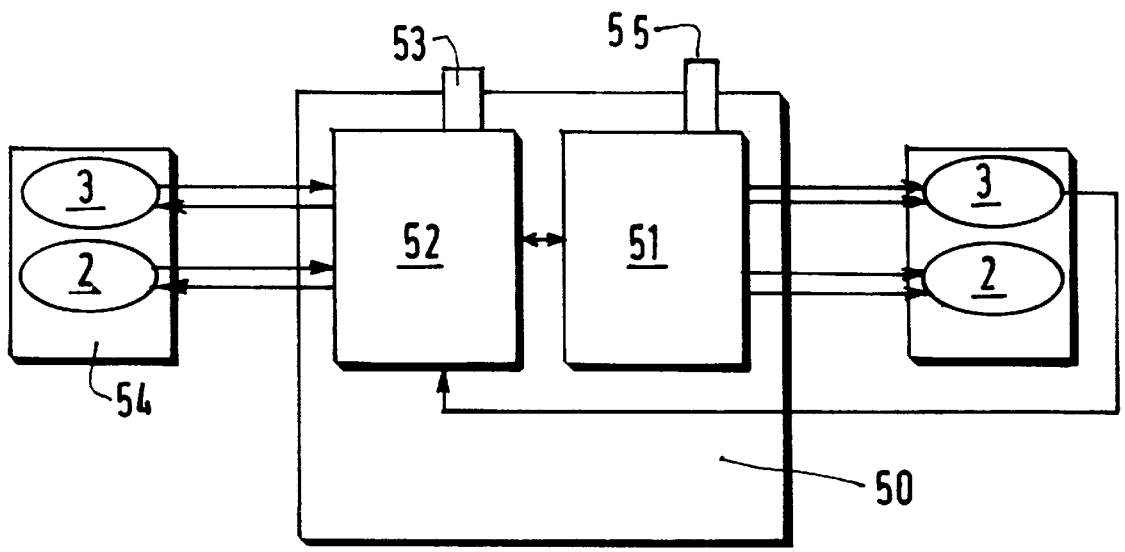
FIG. 5 is a diagram of the electronic stage for controlling the injector.

It will readily be understood that forwards and/or backwards movement of the motor 3 inside the sheath 32 depends on the direction of rotation of the drive shaft, which in turn depends on the sign of the DC power supply under the control of an electronic card 50 (FIG. 5).

FIG. 4 is on a larger scale and in section, and it shows how the cartridge is mounted in the endpiece or housing 10. This figure shows the front end of the piston 6, the cartridge 5 closed at its rear end by a flexible disk 4, e.g. made of neoprene, and bearing against the inside surface of the cartridge 5 so as to be sealed relative thereto. By way of example, the endpiece or housing 10 is screwed onto the body 1 of the injector and constitutes a housing for a needle carrier 43. The front: portion of the piston 6 that is to penetrate into the cartridge 5 carries an O-ring 40. The rear of the cartridge 5 is held in a bearing 41 by a second O-ring 42 which is compressed so as to provide effective guidance for the rear of the cartridge when it is rotated under drive from the motor 2.

Such an injector operates as follows. Initially, under the pressure applied by the dental surgeon, the needle 9 passes through the mucous membrane and its front end comes into contact with bone. In this position, the control circuit serves to power the motor 2, thereby causing its drive shaft to rotate and consequently causing the piston 6, the cartridge 5, and the needle 9 to rotate. This makes it possible to pass through the bone so that the front end of the needle comes into contact with the marrow. The motor 2 is then stopped and the motor 3 is powered so as to cause the anesthetic contained in the cartridge to be injected. After this the direction of rotation of the motor 2 is reversed and the needle 9 is withdrawn from the jaw.

It is thus possible to exert axial thrust that is regulated by the displacement of the motor 3 rotating at low speed. The displacement of the screw 12 in the slot 7 prevents relative rotation.

FIG. 5 is a diagram of the electronic circuit for controlling the injector. It essentially comprises an electronics card 50 having a control stage 51 and a monitoring stage 52. The electronics card serves to control the operation of DC motors 2 and 3, with both motors always rotating in the same direction. Direction of rotation is controlled either automatically as a function of the position and the torque of the injection motor 3, or else manually by pressing against a return button. The current drawn by the injection motor is measured continuously. Thus, if during injection the torque reaches a predetermined value, e.g. 40daN, which corresponds to injection into hard bone, the control circuit 51 immediately reverses the current flow direction for two seconds.

When the card is switched on, the injection motor is automatically returned to its rear position and thereafter its position is known at: all times by calculation as performed by a microprocessor. The injector is protected by an end-of-stroke contact (not shown). In the final stage of injection, once 90% of the anesthetic has been injected, an increase in the current drawn causes the motor 3 to be stopped and returned to its initial position. While it is returning to its initial position, the motor is stopped if ever excess electricity consumption is detected.

The surgeon has an injection control; a rotation control; an ON/OFF switch; a pushbutton 53 for selecting the quantity of substance to be injected; and a manual return button 55 for returning the motor 3 into its initial position. The motors are preferably under foot control via a pair of pedals 54 connected to the monitoring stage 52 and having two surfaces for pressing, one for switching on the rotary drive motor 2, and the other for controlling injection by means of the motor 3.

The key 53 serves to perform prior selection of the quantity of substance that is to be injected, i.e. it displaces the injection motor 3. One press corresponds to 25% of the total quantity, two presses to 50%, three presses to 75%, and four presses to 100%. The amount selected is displayed by light-emitting diodes (not shown). As mentioned above, it is desirable for the speed of injection to vary progressively, which means that the linear displacement of the motor 3 should be accelerated displacement.

Figure 6:
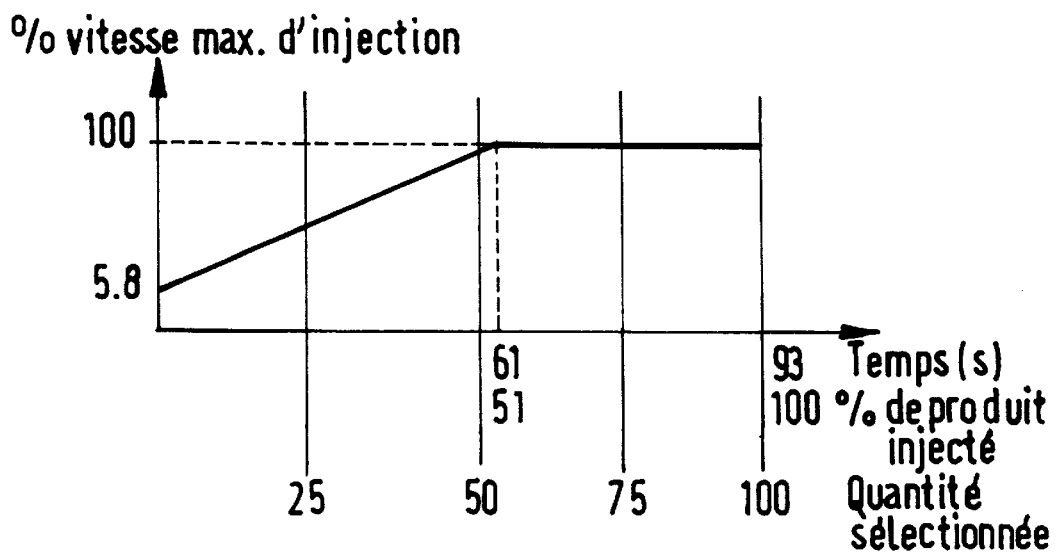
FIG. 6 is a graph showing how injection speed varies as a function of time in order to make injection painless.

FIG. 6 is a graph where the abscissa represents time and the ordinate represents injection speed varying over the range 0to 100%. It has been found that the pain caused by injecting anesthetic comes essentially from injection being performed suddenly after the cortical substances has been perforated. Because of the presence of the electronics card 50, it is possible to regulate injection so it takes place progressively, and therefore without causing pain. As can be seen in the graph, injection speed begins at 5.8% and reaches 100%, i.e. the maximum injection speed, after about 50% of the anesthetic has been injected. The bottom scale graduated from 25to 100represents the quantity of anesthetic to be injected as selected by the button 53.

The injector of the invention can also be used for injecting into soft tissue through which vessels of various sizes pass. It is then necessary to verify that the end of the needle is not in an artery or a vein. In dentistry, this happens when anesthesia is being implemented in the mandible in the vicinity of the SPIX spine. The injector must then be capable of performing suction.

To perform this verification, the end of the cartridge-carrying tube 43 is made of a transparent plastics material such as polycarbonate (which can be sterilized at 130° C.). In parallel, the microprocessor is programmed to make it possible, after two successive presses on the "quantity" key 53 to return the piston, whereas in the preceding embodiment, only automatic return is possible. The O-ring 40 situated at the front end of the piston 6 causes the cartridge to rotate and establishes sealing between the rubber piston 4 of the anesthetic cartridge and the rotary piston 6 so as to secure the two pistons one to the other. If the piston 6 moves backwards, it takes the piston 4 of the cartridge with it, thereby establishing suction which causes an inflow of blood if the end of the needle is in a vessel. This inflow can be seen because the tube carrying the cartridge is transparent.

Naturally, numerous variants can be provided without going beyond the ambit of the invention, in particular by substituting with equivalent technical means.

What is claimed is:

1. An injector, comprising:

an elongated body;

a piston movable longitudinally in the body;

a first motor for driving said piston in a longitudinal direction in the body, wherein the first motor has a drive shaft and is mounted between the body and the piston by at least one threaded part engaged in at least one threaded opening such that operation of the first motor threadably moves the piston longitudinally;

a second motor mounted between the body and said piston, the second motor rotating said piston about a longitudinal axis;

a cartridge defining a space for holding liquid, the cartridge being mounted in the body and closed in part by a movable end wall, the piston being engaged to move said end wall longitudinally relative to the body by operation of the first motor and to rotate the cartridge relative to the body by operation of the second motor, wherein said cartridge is fixed to the body in a longitudinal direction and is rotatable relative to the body;

a controller comprising an electronic control card with a control stage, a monitoring stage, a selection button, a switch and at least one pedal controlling said first motor and said second motor wherein said electronic control card is coupled to a control and returns the piston after two successive operations of the control;

wherein said first motor, said second motor, said cartridge, and said piston are located along a same longitudinal axis.

2. An injector according to claim 1, wherein the threaded part of the first motor comprises an externally threaded screw fixed on the drive shaft and engaged in a threaded opening of the body.

3. An injector according to claim 1, wherein said first motor is held against rotation relative to the body by a screw matingly engaged in a slot extending longitudinally along the body.

4. An injector according to claim 1, wherein the movable end wall of the cartridge comprises a plastic material.

* * * * *